United States Patent [19]

Burnes et al.

[11] Patent Number: 4,515,759
[45] Date of Patent: May 7, 1985

[54] PROCESS OF REMOVING HYDROGEN SULFIDE FROM GAS MIXTURES

[75] Inventors: Edward E. Burnes, Arroyo Grande, Calif.; Kishan Bhatia, Katy, Tex.

[73] Assignee: NL Industries, Inc., New York, N.Y.

[21] Appl. No.: 549,274

[22] Filed: Nov. 3, 1983

[51] Int. Cl.$^3$ ............................................. B01D 53/34
[52] U.S. Cl. ................................. 423/220; 423/223; 423/232; 423/573 R
[58] Field of Search ............... 423/210, 220, 223, 224, 423/234, 385, 573, 6, 573 R; 422/4, 5

[56] References Cited

U.S. PATENT DOCUMENTS

| 676,209 | 6/1901 | Strache | 423/573 |
|---|---|---|---|
| 2,665,190 | 1/1954 | Congdon | 423/241 |
| 3,754,074 | 8/1973 | Grantham | 423/210.5 |
| 4,151,263 | 4/1979 | Ciuryla | 423/242 |

FOREIGN PATENT DOCUMENTS 422726 12/1925 Fed. Rep. of Germany .

OTHER PUBLICATIONS

C.A. 88, 65471 (1978).

Primary Examiner—Earl C. Thomas
Attorney, Agent, or Firm—Browning, Bushman, Zamecki & Anderson

[57] ABSTRACT

Process for the removal of hydrogen sulfide from gas mixtures, particular gas mixtures containing hydrocarbons, wherein the gas mixture is treated with an aqueous solution of a water soluble nitrite such as sodium nitrite, the pH of the aqueous solution being at least 5.5 or greater.

9 Claims, No Drawings

PROCESS OF REMOVING HYDROGEN SULFIDE FROM GAS MIXTURES

BACKGROUND OF THE INVENTION

The present invention relates to the removal of hydrogen sulfide from gas mixtures, particularly gas mixtures containing hydrocarbons such as, for example, natural gas.

The removal of $H_2S$ from a gas stream is a problem that has long confronted and challenged workers in many diverse industries. One prime example is in the natural gas industry where the $H_2S$ content of certain gas streams recovered from natural gas deposits in many areas of the world is too high for commercial acceptance. Over and above the environmental and safety hazards posed by the presence of $H_2S$ in natural gas streams, the presence of such sulfur-containing compounds may result in the deposition of sulfur salts which can cause plugging and corrosion of transmission pipes, valves, regulators and the like. Even if the natural gas is flared as a waste stream, it is necessary that the $H_2S$ either be completely removed or at least reduced to a level where the combustion products from the flaring do not introduce deleterious amounts of pollutants such as, for example, $SO_2$, an ingredient of "acid rain."

The "sweetening" or removal of $H_2S$ from natural gas is only one example of where $H_2S$ removal must be accomplished. In the manufactured gas industry or the coke-making industry, coal gas containing unacceptable amounts of $H_2S$ is commonly produced by the destructive distillation of bituminus coal having high sulfur content. Another $H_2S$ contamination problem is found in the manufacture of water gas or synthesis gas where it is not unusual to produce gas streams containing $H_2S$ by passing steam over a bed of incandescent coke or coal containing a minor amount of sulfur. $H_2S$ removal is also a frequently encountered problem in the petroleum refining industry because the principal raw material used, crude oil, typically contains minor amounts of sulfur—principally in the form of organic sulfur compounds. During the course of the many processes to which the crude oil or fractions thereof are subjected, one or more gas streams containing $H_2S$ are quite commonly produced.

Regardless of the source of the gas stream, the problem of removing $H_2S$ therefrom has been solved in numerous different ways which generally involve one or more of the following techniques: selective absorption with a wide variety of absorbents; absorption by suitable absorbent; and selective reaction with a reagent which produces an easily separable product. The details of these techniques are well known to those skilled in the art. The voluminous number of prior art processes, patents and publications dealing with the removal of $H_2S$ from gas mixtures testifies to two facts: (1) the desirability, and in most cases, the necessity of removing the $H_2S$ from the gas streams; and (2) that heretofore no completely desirable process has been found.

It is known that nitrous acid and nitrites, most commonly employed as oxidizing agents, can react in aqueous solutions with hydrogen sulfide to produce various oxidation products depending upon the pH. However, heretofore, it has not been proposed to remove hydrogen sulfide from gas mixtures, for example natural gas streams, by treating the gas mixture with an aqueous scrubbing or treating medium utilizing a water soluble nitrite.

SUMMARY OF THE INVENTION

It is therefore an object of the present invention to provide a novel process for the removal of $H_2S$ from gas mixtures.

Another object of the present invention is to provide a process for the removal of $H_2S$ from gas mixtures in which the production of undesirable by-products is minimized.

Yet another object of the present invention is to provide a method for the removal of $H_2S$ gas mixtures in which the $H_2S$ by-products are relatively easily subjected to disposal.

The above and other objects of the present invention will become apparent from the description given herein and the claims.

The process of the present invention comprises treating, e.g., scrubbing, a gas mixture containing hydrogen sulfide with an aqueous medium containing an effective amount of a water soluble nitrite, the pH of the aqueous medium being about 5.5 or greater, preferably from about 6 to about 10.

DESCRIPTION OF THE PREFERRED EMBODIMENT

Gas mixtures particularly suited to removal of $H_2S$ according to the process of the present invention are naturally occurring gases, synthesis gases, process gases and fuel gases produced by gasification procedures, e.g. gases produced by the gasification of coal, petroleum, shale, tar sands, etc. Particularly preferred are natural gas streams, cold gasification streams and refinery feed stocks composed of gaseous hydrocarbon streams and other gaseous hydrocarbon streams. The term "natural gas" or "natural gas stream," as used herein, refers to a mixture of gases comprising primarily methane with smaller amounts of at least the following components: nitrogen, carbon monoxide, carbon dioxide and ethane. The term "hydrocarbon stream(s)", as employed herein, is intended to include streams containing significant quantities of hydrocarbon (both paraffinic and aromatic), it being recognized that such streams contain significant "impurities" not technically defined as a hydrocarbon. Again, streams containing principally a single hydrocarbon, e.g. methane, are eminently suited to the practice of the present invention. Streams derived from the gasification and/or partial oxidation of gases or liquid hydrocarbons may be treated by the invention. Indeed, the process can be used with any gas stream containing $H_2S$ that does not contain components which will selectively react, to any appreciable degree, with the active component of the scrubbing medium, i.e. the soluble nitrite. The $H_2S$ content of the type of stream contemplated will vary extensively, but, in general, will range from about 0.01 percent to about 15 percent by volume. Obviously, the content of $H_2S$ and the gaseous mixture is not a limiting factor in the practice of the process of the present invention.

The process of the present invention utilizes an aqueous medium, which may be considered a scrubbing or contacting medium, containing a water soluble nitrite. The term "aqueous medium" is intended to include solutions as well as slurries or other aqueous mixtures. Indeed, as the treatment of the gas mixture containing the $H_2S$ proceeds according to the process of the present invention, elemental sulfur is often formed so that the aqueous medium, while it may initially be a true solution becomes a slurry containing the soluble, unreacted nitrite, various oxidation products of the hydrogen sulfide and particulate, elemental sulfur. The soluble nitrites useful in the process of the present invention, generally speaking, are the alkali and alkaline-earth metal nitrites such as, for example, sodium nitrite, potassium nitrite, lithium nitrite, calcium nitrite, magnesium nitrite, etc. Such metal nitrites are characterized by high solubility in water and, in the case of sodium nitrite, are relatively inexpensive. Heavy metal nitrites, while they will function, are less desirable because of their greatly reduced solubility in water. Moreover, heavy metal nitrites are somewhat more hazardous to handle since thermally, they are much less stable than the alkali and alkaline-earth metal nitrites. Particularly preferred because of their ready availability and high solubility are the alkali metal nitrites, particularly sodium nitrite.

The concentration of the water soluble nitrite in the aqueous medium can vary widely depending upon the $H_2S$ concentration of the gaseous mixture, the desired degree of $H_2S$ removal, the volume of gaseous mixture being treated, and other such parameters. In general, only an effective amount need be present, although in the preferred case, the water soluble nitrite will be present in an amount of from about 0.1 percent to about saturation, more particularly from about 5 to about 40 percent by weight, calculated as nitrite.

In conducting the process of the present invention, it is necessary that the pH be maintained above about 5.5, preferably above 7. At a lower pH, the nitrite decomposes leading to utilization of the active nitrite and the formation of excessive amounts of nitrogen oxides ($NO_x$). Additionally, $SO_2$ is formed at lower pH values and is vented in the effluent gas. Since the pH of an aqueous solution (10–30 percent by weight) of an alkali metal or alkaline-earth metal nitrite is generally from about 6 to about 8, it will be appreciated that a buffering agent is not necessary. However, the presence of a buffering agent which will maintain the aqueous medium at a pH of at least 7 to about 10 is desirable as it minimizes large swings in the pH which can affect the efficiency of the process. For example, $CO_2$ and other acid gases commonly present in streams containing $H_2S$ are more readily absorbed at high pH values. On the other hand, a buffering agent will also help to prevent a rapid lowering of pH should an acid contaminant unexpectedly be introduced into the system and which, in the absence of the buffer, would lower the pH to below about 5 thereby resulting in the decomposition of the soluble nitrite and formation of $SO_2$. Non-limiting examples of suitable buffering agents include borates such as sodium borate; phosphates, such as potassium dihydrogen phosphate; bicarbonates, such as sodium bicarbonate; phthalates, such as potassium hydrogen phthalate; ammonium chloride buffers and mixtures thereof. It will be understood that such buffering agents will be admixed with the requisite amounts of various acids and bases to obtain the desired pH. Non-limiting examples of suitable buffering agents and methods and preparation therefor as set forth in "Buffer Solutions Operational Definitions of pH," R.A. Robinson, *Handbook of Physics and Chemistry*, 61st Edition, incorporated herein by reference.

The "treatment" of gaseous mixture containing $H_2S$ contemplates any method by which the gaseous mixture is brought into intimate contact with the aqueous or scrubbing medium containing the water soluble nitrite. Thus, the gaseous mixture may be contacted with the aqueous medium in any conventional gas-liquid contactor. For example, the aqueous medium may be sprayed over the gas mixture or a packed tower may be used. The gas may be bubbled through a vessel containing the aqueous medium or the gas mixture and aqueous medium may be contacted in a countercurrent gas-liquid extractor. It will be readily apparent to those skilled in the art that many other methods of effecting treatment or scrubbing of the gas mixture with the aqueous medium can be employed. Therefore, any conventional manner of contacting found convenient and efficient is suitable for the operation of the invention.

The particular method of treatment of the gaseous mixture, whether it be referred to as contacting, scrubbing or the like, should be such as to permit a contact time between the gaseous mixture and the aqueous medium sufficiently long to ensure reaction of the water soluble nitrite with the $H_2S$. It will be appreciated that the contact time can vary considerably depending upon $H_2S$ content, gas flow rate, volume of aqueous scrubbing medium, etc. In general, however, contact times ranging from about 0.01 second to about 270 seconds or longer can be employed.

Temperatures employed in the process of the present invention are generally not critical with the exception that the temperature be kept below the melting point of sulfur, one of the conversion by-products of the $H_2S$. From a practical point of view, the process is generally conducted at ambient temperatures, temperatures of from 10° C. to 80° C. being suitable, temperatures from 20° C. to 45° C. being preferred.

Pressure conditions in the process may vary widely. For example, pressures in the process may vary from one atmosphere up to several hundred atmospheres, pressures of from about one atmosphere up to about 50 atmospheres being preferred, particularly in the case of natural gas streams. The pressure-temperature relationships involved in gas-liquid contacting and scrubbing processes are well understood by those skilled in the art, and need not be detailed herein.

As is well known, gas mixtures which contain $H_2S$ as an impurity also generally contain $CO_2$, the latter component generally being present in amounts greater than the $H_2S$. In many systems designed to remove $H_2S$ from gas mixtures, the presence of $CO_2$, particularly in relatively large amounts, poses a particularly acute problem since the $CO_2$ will react with and hence deplete the active component which is also used to remove the $H_2S$. Thus, for example, in the case of the removal of $H_2S$ from sour natural gas streams utilizing alkaline liquids, e.g. caustic soda, appreciable absorption of $CO_2$ rapidly diminishes the concentration of the alkaline scrubbing agent. It is a particular feature of the present invention that the presence of relatively large amounts of $CO_2$ in the gaseous mixture is not significantly detrimental to the present process in terms of loss of active nitrite. At preferred pH levels, reaction between dissolved $CO_2$ and nitrite ion is relatively inconsequential with the result that minimal active agent, e.g. soluble nitrite, is used up by $CO_2$ absorption. As pointed out above, the process of the present invention is advantageously carried out in the presence of a buffering agent. As is well known, the absorption of $CO_2$ in an aqueous solution will result in the formation of bicarbonate ions. Accordingly, the presence of $CO_2$ in the gas mixture being treated according to the process of the present invention results in the in situ formation of a buffering agent inasmuch as, as the treatment progresses, the bicarbonate concentration increases and hence the buffering action increases.

In order to more fully illustrate the present invention, the following non-limiting examples are presented.

In Examples 1–13 which follow, the following procedure was employed. A one liter jar approximately seven inches tall and having a cross-sectional area of approximately 9 sq. in. was charged with sufficient aqueous medium containing water soluble nitrite to provide a liquid column height in the jar of approximately 5-½ in. A sparger tube was disposed in the jar and spaced from the bottom approximately one-half inch so as to permit approximately 5 in. of vertical contact between the gas exiting from the bottom of the sparger tube and the liquid column. During the scrubbing procedure, the aqueous medium was continuously stirred with a magnetic stirrer and flow rate, pH and effluent gas composition were periodically determined. Pressure and temperature conditions were ambient and all gas measurements were made with standard Drager tubes. The gas employed had the following composition (by volume):
1% $H_2S$
5% $CO_2$
94% $CH_4$.

EXAMPLE 1

In this example, the aqueous medium which had an initial pH of 9.3, consisted of 80 g of sodium nitrite dissolved in 720 g of deionized water. The results are given in Table 1 below.

TABLE 1

| Time (min) | pH | Effluent Gas Composition (ppm) | | | Flow Rate (SCF/hr) |
|---|---|---|---|---|---|
| | | $H_2S$ | $CO_2$ | $NO_x$ | |
| 2 | 6.5 | 1,800 | | | |
| 8 | | | | 20 | |
| 14 | | | 30,000 | | |
| 19 | | 1,200 | | | |
| 21 | | | | 15 | 2 |
| 22 | | | | | |
| 28 | | 1,300 | | | |
| 34 | | | 30,000 | | |
| 36 | 6.7 | | | | |
| 50 | 6.8 | | | 13 | 2 |
| 57 | | 2,000 | | | |
| 59 | | | 30,000 | | 4 |
| 63 | | | 45,000 | | |
| 103 | 6.9 | | | | |

EXAMPLE 2

In this example, the aqueous medium, which had an initial pH of 8.95, consisted of 80 g of sodium nitrite, 16 g of sodium borate (buffer) and 704 g of deionized water. The results are given in Table 2 below.

TABLE 2

| Time (min) | pH | Effluent Gas Composition (ppm) | | | Flow Rate (SCF/hr) |
|---|---|---|---|---|---|
| | | $H_2S$ | $CO_2$ | $NO_x$ | |
| 2 | 9.0 | | | | |
| 4 | | | | | 4.0 |
| 5 | | | 15,000 | | |
| 7 | 8.90 | 50 | | | |
| 8 | 8.80 | 160 | | | |
| 10 | 8.70 | | | 3.0 | |
| 12 | 8.65 | | 25,000 | | |
| 16 | 8.50 | | | | |
| 18 | 8.40 | | 8,000 | | |
| 20 | 8.35 | 1,000 | | | |

TABLE 2-continued

| Time (min) | pH | Effluent Gas Composition (ppm) | | | Flow Rate (SCF/hr) |
|---|---|---|---|---|---|
| | | $H_2S$ | $CO_2$ | $NO_x$ | |
| 22 | 8.30 | | | 1.0 | 4.5 |
| 30 | 8.10 | 1,400 | 10,000 | | |
| 31 | | | | | 8.0 |
| 32 | 8.07 | | 30,000 | | |
| 33 | 8.05 | 900 | | | |
| 38 | 8.00 | | | 3.0 | |
| 44 | 7.96 | 2,000 | 30,000 | | 9.0 |
| 51 | 7.83 | 5,000 | | | |
| 54 | 7.80 | | 38,000 | | |
| 60 | 7.80 | | | 5.0 | 9.0 |

Although the aqueous medium remained clear during the scrubbing process, it was noted that a precipitate of sulfur appeared about thirty minutes after the reaction was stopped.

EXAMPLE 3

The aqueous medium used in this example consisted of 80 g sodium nitrite, 16 g sodium bicarbonate (buffering agent) and 704 g of deionized water, and had an initial pH of 7.86. The results are given in Table 3 below.

TABLE 3

| Time (min) | ph | Effluent Gas Composition (ppm) | | | Flow Rate (SCF/hr) |
|---|---|---|---|---|---|
| | | $H_2S$ | $CO_2$ | $NO_x$ | |
| 1 | | | 20,000 | | 8.0 |
| 2 | | 1,800 | | | |
| 5 | 8.02 | | | 5 | |
| 13 | 8.15 | | | | |
| 17 | 8.18 | | 25,000 | | |
| 19 | 8.17 | 3,100 | | | |
| 21 | 8.17 | | | 3 | |
| 30 | 8.20 | | 23,000 | | |
| 32 | 8.20 | 4,400 | | | |
| 36 | 8.20 | | | 4 | |
| 56 | 8.22 | 4,400 | | | |
| 58 | 8.22 | | 37,000 | | |
| 60 | 8.22 | | | 17 | |

EXAMPLE 4

In this example, which shows the effect of high gas flow rates and no buffering agent, the aqueous medium, which had an initial pH of 9.31, consisted of 80 g of sodium nitrite and 720 g of deionized water. The results are given in Table 4 below.

TABLE 4

| Time (min) | pH | Effluent Gas Composition (ppm) | | | Flow Rate (SCF/hr) |
|---|---|---|---|---|---|
| | | $H_2S$ | $CO_2$ | $NO_x$ | |
| 1 | 6.49 | | 38,000 | | 8 |
| 2 | 6.40 | 4,400 | | | |
| 5 | 6.53 | | | 3.0 | |
| 9 | 6.56 | | | | |
| 15 | 6.60 | 4,400 | 40,000 | | |
| 18 | 6.60 | | | 3.0 | 8 |
| 25 | 6.67 | | | | |
| 30 | 6.70 | | 38,000 | | |
| 31 | 6.70 | 4,400 | | | |
| 35 | 6.73 | | | 3.0 | |
| 40 | 6.75 | | | | |
| 50 | 6.78 | | | | |
| 55 | 6.80 | | | | |
| 60 | 6.82 | 5,000 | 30,000 | | 8 |
| 63 | | | | 3.0 | |

It was noted that at approximately two minutes into the run, a precipitate of elemental sulfur formed.

EXAMPLE 5

This example demonstrates the effect of using a citric acid buffer at relatively high gas flow rates. The aqueous medium was prepared by dissolving 80 g of sodium nitrite in 720 g of deionized water and adding 0.5 ml of a 10% aqueous citric acid solution. The initial pH of the aqueous medium was 6.0. The results are given in Table 5 below.

TABLE 5

| Time (min) | pH | Effluent Gas Composition (ppm) | | | Flow Rate (SCF/hr) |
|---|---|---|---|---|---|
| | | $H_2S$ | $CO_2$ | $NO_x$ | |
| 3 | 6.1 | | 30,000 | | 8.0 |
| 4 | 6.2 | 5,000 | | | |
| 10 | 6.5 | 4,000 | | | |
| 12 | 6.5 | | 28,000 | | |
| 13 | 6.5 | | | 3.0 | |
| 20 | 6.6 | | | | |
| 30 | 6.70 | 4,000 | 30,000 | | |
| 33 | 6.66 | | | 3.0 | 8.0 |
| 38 | 6.72 | | | | |
| 45 | 6.75 | 4,400 | | | |
| 46 | 6.75 | | 33,000 | | |
| 49 | 6.74 | | | 3.0 | 8.0 |
| 55 | 6.80 | | | | |
| 60 | | | | | |
| 62 | 6.82 | 4,100 | 37,000 | 3.0 | 8.0 |

At four minutes it was noted that a precipitate of elemental sulfur formed.

EXAMPLE 6

In this example, the aqueous scrubbing medium consisted of 80 g of sodium nitrite, 16 g of ammonium chloride and 704 g of deionized water. To this solution was added 3 ml of 30 percent ammonium hydroxide to provide a buffered solution having an initial pH of 8.97. The results are given in Table 6 below.

TABLE 6

| Time (min) | pH | Effluent Gas Composition (ppm) | | | Flow Rate (SCF/hr) |
|---|---|---|---|---|---|
| | | $H_2S$ | $CO_2$ | $NO_x$ | |
| 2 | 8.85 | | 32,000 | | 8.0 |
| 3 | 8.65 | 800 | | | |
| 6 | 8.50 | | | 1.0 | 8.0 |
| 11 | 8.27 | | | | |
| 15 | 8.13 | 6,000 | | | |
| 16 | 8.10 | | 35,000 | | |
| 18 | 8.00 | | | 5.0 | |
| 25 | 7.80 | | | | |
| 30 | 7.70 | 6,100 | | | |
| 31 | 7.66 | | 34,000 | | |
| 32 | 7.76 | | | 5.0 | 8.0 |
| 40 | 7.62 | | | | |
| 43 | 7.62 | 4,000 | | | |
| 47 | 7.62 | | 30,000 | | |
| 60 | 7.62 | 3,700 | 28,000 | | |
| 62 | | | | 6.0 | |

EXAMPLE 7

The aqueous scrubbing medium used in this example consisted of 80 g sodium nitrite, 40 g of sodium borate (buffer) and 702 g of deionized water. It was noted that the sodium borate did not completely dissolve and a certain portion remained undissolved throughout the run. The initial pH of the aqueous medium was 9.02. The results are given in Table 7 below.

TABLE 7

| Time (min) | pH | Effluent Gas Composition (ppm) | | | Flow Rate (SCF/hr) |
|---|---|---|---|---|---|
| | | $H_2S$ | $CO_2$ | $NO_x$ | |
| 2 | 8.95 | 100 | | | |
| 4 | 8.90 | | 7,000 | | |
| 8 | | | | (200) | |
| 22 | 8.51 | | 5,000 | | |
| 23 | 8.50 | 800 | | | |
| 25 | 8.47 | | | 20 | 2 |
| 26 | 8.47 | 900 | | | |
| 35 | 8.37 | | | | |
| 55 | 8.17 | 1,600 | | | |
| 58 | | | 5,000 | | |
| 71 | 8.16 | | 5,000 | | |
| 73 | 8.09 | | | 8 | 2 |
| 86 | 8.05 | | | | |
| 89 | 8.03 | | 6,000 | | |
| 90 | 8.03 | 1,800 | | | |
| 91 | 8.03 | | | 10 | |
| 111 | 7.99 | | 8,000 | | |
| 114 | 7.96 | 1,500 | | | |
| 115 | 7.95 | | | 15 | |

EXAMPLE 8

In this example, the aqueous medium consisted of 80 g of sodium nitrite, 40 g of sodium bicarbonate (buffer) and 680 g of deionized water. The initial pH of the aqueous medium was 7.96. The results are given in Table 8 below.

TABLE 8

| Time (min) | pH | Effluent Gas Composition (ppm) | | | Flow Rate (SCF/hr) |
|---|---|---|---|---|---|
| | | $H_2S$ | $CO_2$ | $NO_x$ | |
| 2 | 8.04 | | 20,000 | | 2 |
| 3 | 8.06 | 200 | | | |
| 4 | 8.11 | | | 13 | |
| 32 | 8.33 | 900 | | | |
| 35 | 8.34 | | 13,000 | | |
| 36 | 8.34 | | | 10 | 2 |
| 64 | 8.46 | | | | |
| 65 | 8.46 | 900 | | | |
| 66 | 8.46 | | 10,000 | | |
| 67 | 8.46 | | | 20 | 2 |
| 96 | 8.45 | | | | |
| 97 | 8.45 | 1,400 | 10,000 | 20 | 2 |
| 117 | 8.55 | 1,000 | | | |
| 119 | 8.56 | | 11,000 | | |
| 121 | 8.56 | | | 20 | 2 |

It was noted that after about 96 minutes, a small amount of sulfur precipitate formed.

EXAMPLE 9

The aqueous medium used in this example consisted of 80 g of sodium nitrite dissolved in 680 g of deionized water to which was added 40 g of ammonium chloride. To this solution was added 5 ml of 30 percent ammonium hydroxide solution to provide a buffered aqueous medium having an initial pH of 9.0. The results are given in Table 9 below.

TABLE 9

| Time (min) | pH | Effluent Gas Composition (ppm) | | | Flow Rate (SCF/hr) |
|---|---|---|---|---|---|
| | | $H_2S$ | $CO_2$ | $NO_x$ | |
| 2 | 8.95 | | 2,000 | | 2 |
| 3 | 8.95 | 100 | | | 2 |
| 5 | 8.90 | | | 200 | |
| 30 | 8.55 | 1,000 | | | |
| 32 | 8.55 | | 5,000 | | |
| 33 | 8.55 | | | 12 | |

TABLE 9-continued

| Time (min) | pH | Effluent Gas Composition (ppm) | | | Flow Rate (SCF/hr) |
|---|---|---|---|---|---|
| | | H$_2$S | CO$_2$ | NO$_x$ | |
| 58 | 8.34 | 1,700 | 5,000 | | 2 |
| 61 | 8.32 | | | 10 | |
| 90 | 8.14 | 1,600 | 7,000 | | |
| 92 | | | | | |
| 93 | 8.13 | | | 10 | |
| 119 | 8.06 | 1,200 | | | |
| 120 | 8.07 | | 6,000 | | |
| 121 | | | | 12 | |

It was noted that after 33 minutes the solution turned a pale yellow, and after about 117 minutes, a small amount of a sulfur precipitate formed.

EXAMPLE 10

The buffered aqueous medium employed in this example consisted of 82.5 g of sodium nitrite, 16.0 g of sodium borate and 708.5 g of water. The initial pH of the aqueous medium was 8.88. The results are given in Table 10 below.

TABLE 10

| Time (min) | pH | Effluent Gas Composition (ppm) | | | Flow Rate (SCF/hr) |
|---|---|---|---|---|---|
| | | H$_2$S | CO$_2$ | NO$_x$ | |
| 3 | | | 5,200 | | |
| 4 | | 100 | | | |
| 6 | | | | 10 | 2 |
| 12 | 8.69 | | | | |
| 30 | 8.35 | | | | |
| 34 | 8.27 | | 7,000 | | |
| 35 | | 1,000 | | | |
| 36 | | | | 15 | 2 |
| 50 | 8.08 | | | | |
| 60 | 8.00 | | | | |
| 61 | | | 7,000 | | |
| 62 | | 1,400 | | | |
| 63 | 7.96 | | | 8 | 2 |
| 100 | 7.81 | | 9,000 | | |
| 102 | | 1,500 | | | |
| 103 | 7.80 | | | 10 | 2 |
| 122 | 7.81 | | 11,000 | | |
| 124 | 7.81 | 1,000 | | | |
| 125 | | | | 10 | |

After approximately 100 minutes, a small amount of a sulfur precipitate began to form.

EXAMPLE 11

In this example, the aqueous scrubbing medium consisted of 81.5 g of sodium nitrite, 16.0 g of ammonium bicarbonate and 704 g of water. The initial pH of the scrubbing medium was 8.01. The results are given in Table 11 below.

TABLE 11

| Time (min) | pH | Effluent Gas Composition (ppm) | | | Flow Rate (SCF/hr) |
|---|---|---|---|---|---|
| | | H$_2$S | CO$_2$ | NO$_x$ | |
| 3 | | | 13,000 | | |
| 4 | 8.05 | 200 | | | |
| 5 | | | | 20 | 2 |
| 30 | 8.15 | | 11,000 | | |
| 32 | 8.15 | 900 | | | |
| 34 | | | | 20 | 2 |
| 70 | 8.20 | | 12,000 | | |
| 73 | 8.20 | 900 | | | |
| 75 | | | | 40 | 2 |
| 90 | 8.23 | | 12,000 | | |
| 91 | | 1,000 | | | |
| 92 | | | | 20 | 2 |

TABLE 11-continued

| Time (min) | pH | Effluent Gas Composition (ppm) | | | Flow Rate (SCF/hr) |
|---|---|---|---|---|---|
| | | H$_2$S | CO$_2$ | NO$_x$ | |
| 120 | 8.26 | | 12,000 | | |
| 121 | | 800 | | | |
| 122 | | | | 25 | 2 |

It was noted that after the run was completed, there was no precipitate present in the scrubbing vessel, although the solution had an orange color.

EXAMPLE 12

In this example, the scrubbing medium consisted of 80.0 g of sodium nitrite, 16.0 g of ammonium chloride and 704 g of deionized water to which was added 2 ml of 30 percent ammonium hydroxide to provide a buffered aqueous scrubbing medium with an initial pH of 9.0. The results are given in Table 12 below.

TABLE 12

| Time (min) | pH | Effluent Gas Composition (ppm) | | | Flow Rate (SCF/hr) |
|---|---|---|---|---|---|
| | | H$_2$S | CO$_2$ | NO$_x$ | |
| 3 | | 150 | 6,000 | | |
| 5 | | | | 3 | |
| 32 | 8.15 | | 10,000 | | |
| 38 | 8.03 | 1,200 | | 12 | 2 |
| 67 | 7.76 | 800 | 10,000 | | |
| 73 | 7.75 | | | 12 | 2 |
| 92 | | | 9,000 | | |
| 94 | 7.77 | 800 | | | |
| 99 | 7.77 | | | 13 | 2 |
| 127 | 7.77 | | 10,000 | | |
| 130 | | 800 | | | |
| 132 | | | | 15 | 2 |

After approximately 122 minutes into the run, it was noted that a sulfur precipitate began to form.

EXAMPLE 13

This example shows the effect of conducting the process of the present invention at a lower pH. The aqueous scrubbing medium consisted of 80 g of sodium nitrite dissolved in 720 g of deionized water to which was added sufficient hydrochloric acid to provide an aqueous scrubbing medium with an initial pH of 5.5. The results are given in Table 13 below.

TABLE 13

| Time (min) | pH | Effluent Gas Composition (ppm) | | | | Flow Rate (SCF/hr) |
|---|---|---|---|---|---|---|
| | | H$_2$S | CO$_2$ | NO$_x$ | SO$_2$ | |
| 2 | 5.55 | | 15,000 | | | 2 |
| 3 | 5.60 | 500 | | 400 | | |
| 6 | 5.80 | | | | 300 | |
| 9 | 6.00 | | 10,000 | | | |
| 11 | 6.10 | | | 100 | 100 | |
| 13 | 6.16 | 500 | | | | 2 |
| 16 | 6.23 | | | 40 | 30 | |
| 20 | 6.30 | | | | | |
| 28 | 6.40 | | | | | |
| 29 | 6.40 | | 9,000 | | | |
| 30 | 6.42 | 700 | | | | |
| 32 | 6.43 | | | | 10 | 2 |
| 35 | 6.44 | | | 7 | | |
| 59 | 6.54 | | 9,000 | | | |
| 61 | 6.54 | | | 5 | | |
| 62 | 6.55 | | | | 0 | |
| 63 | 6.56 | 900 | | | | |
| 98 | 6.66 | | 10,000 | | | |
| 99 | | 900 | | | | 2 |
| 101 | 6.67 | | | 6 | 0 | |

TABLE 13-continued

| Time (min) | pH | Effluent Gas Composition (ppm) | | | | Flow Rate (SCF/hr) |
|---|---|---|---|---|---|---|
| | | $H_2S$ | $CO_2$ | $NO_x$ | $SO_2$ | |
| 120 | 6.70 | | 10,000 | | | |
| 121 | | 900 | | 6 | 0 | |

As can be seen, at a pH of 5.5 or lower, there was excessive generation of $NO_x$. Additionally, there was substantial $SO_2$ formed. Upon lowering the pH to 3.7, copious amounts of $NO_x$ evolved. It can thus be seen that to avoid the formation of excessive amounts of $NO_x$ and sulfur dioxide, the pH of the aqueous scrubbing medium should be kept at least above about 5.5, and preferably above 6.

To demonstrate the effectiveness of the process of the present invention in actual field trials, the following examples are presented:

EXAMPLE 14

In this test, conducted at Conoco's Grub Lease Test Site #258, the natural gas stream was heated in a scrubbing vessel having a volume of 1190 gal. filled with 600 gal. of an aqueous scrubbing medium containing 9 percent by weight sodium nitrite and sufficient concentrated citric acid to provide an initial pH of 6.8. Process parameters are shown below:

| | |
|---|---|
| Gas flow rate, mcf/day | 800 |
| Tank volume, gal. | 1,190 |
| Fluid volume, gal. | 600 |
| Gas volume, gal. | 590 |
| Overburden pressure, psi | 100 |
| Fluid pressure drop, psi | 2.3 |
| Sodium nitrite, % by weight | 9 |
| Fluid pH, initial | 6.8 |
| Fluid pH, during test | 6.7 |
| $H_2S$, ppm. (feed) | 7–50 |
| $H_2S$, ppm (effluent) | 0 |
| $CO_2$, vol. % | 0.5 |
| Fluid density, lb/gal. | 8.94 |
| Gas diffusion | Spreader Bar |

The test was conducted for a period of approximately two (2) months during which time the pH remained at about 6.7. $H_2S$ and $CO_2$ concentrations of the feed and effluent gas streams were measured with standard Drager tubes. As can be seen, whereas the feed gas contain $H_2S$ in amounts ranging from 7 to 50 ppm, the effluent gas contained no measurable $H_2S$.

EXAMPLE 15

A second test was conducted at a Gulf Oil leas near Santa Maria, Calif. The aqueous scrubbing medium was prepared as per the procedure of Example 14. The system parameters are given below:

| | |
|---|---|
| Gas flow rate, mcf/day | 80 |
| Tank volume, gal. | 2,940 |
| Gas volume, gal. | 1,140 |
| Fluid pressure drop, psi | 6.17 |
| Fluid density, lb/gal. | 9.70 |
| Gas diffusion | Perforated Disk |
| Sodium nitrite, % by weight | 19.9 |

In this test, the feed gas contained a much higher concentration of $H_2S$ and, accordingly, to test the effectiveness of the method more precisely, the $H_2S$ content of the gas, feed and effluent, were monitored over a 120 hour (5-day) period. The results are given in Table 14 below.

TABLE 14

| Time, hours | 0 | 0.2 | 0.5 | 4.5 | 7.5 | 21 | 24 | 28 | 77 | 120 |
|---|---|---|---|---|---|---|---|---|---|---|
| pH | 8.80 | 7.0 | 7.0 | 7.83 | 7.84 | 7.92 | 7.92 | 7.6 | 7.82 | 7.83 |
| $H_2S$ in, ppm | — | 5720 | 4400 | 7040 | 8020 | 6600 | 6840 | 7040 | 8800 | 8800 |
| $H_2S$ out, ppm | — | 880 | 200+ | 200+ | 180 | 18 | 18 | 80 | 19 | 6 |
| $CO_2$ in, vol. % | — | 5.0 | 3.5 | 3.5 | 3.5 | 4.2 | 3.5 | 3.0 | 4.5 | 5.0 |
| $CO_2$ out, vol. % | — | 2.5 | 2.5 | 2.5 | 3.0 | 2.1 | 2.0 | 2.5 | 2.7 | 3.0 |
| $NO + NO_2$ ($NO_x$) out, ppm | — | 100+ | 100+ | 100+ | 100+ | 100+ | 100+ | 100+ | 100+ | 100+ |
| Overburden, psi | — | 40 | 35 | 40 | 40 | 40 | 60 | 60 | 40 | 40 |
| Fluid vol., gal. | 1800 | 1800 | 1800 | 1800 | 1800 | 1800 | 1800 | 1800 | 900 | 900 |

As can be seen, over a period of five (5) days, the process of the present invention was extremely effective in removing $H_2S$ from the natural gas stream. Note that over the five-day period, the process accomplished greater than 90 percent removal of $H_2S$. Considering that the maximum allowable concentration of $H_2S$ in effluent natural gas streams in the state of Californis is 800 ppm, it can be seen that the process of the present invention is extremely effective. In this regard, it can be seen that after only fifteen minutes of scrubbing, the $H_2S$ content was reduced from 5,720 ppm to 880 ppm.

As can be seen from the examples above, the process of the present invention provides an extremely effective method of removing $H_2S$ from gas mixtures, especially natural gas streams. The process is effective over a wide range of gas flow rates, pH values and concentrations of the water soluble nitrite. Of particular importance is the fact that the by-products of the $H_2S$ removal can be disposed of more readily than by-products from other $H_2S$ removal processes. As is well known, many $H_2S$ removal processes involve the use of slurries such as zinc compounds and produces, as a by-product, zinc sulfide. Zinc sulfide presents a formidable disposal problem. While in some cases, the process of the present invention results in the formation of elemental, solid sulfur, the disposal problems associated with sulfur are significantly less than those associated with a solid such as zinc sulfide. Indeed, elemental sulfur is a raw material in many processes, and hence may be considered a useful and salable by-product of the process. This is particularly true in many underdeveloped countries where adequate, sour natural gas is present but sulfur supplies are in short supply. In such countries, the process could be optimized to maximize the sulfur make and thereby produce a valuable raw material which can be used in the manufacture of fertilizers and other products badly needed in such countries. It should also be observed that, as seen in Table 14, in general, the process of the present invention is not adversely affected by relatively large amounts of $CO_2$ in the feed gas, a problem that has long plagued $H_2S$ removal processes.

Although, as noted above, the oxidation of H₂S by nitrite in an aqueous solution is known, it was unexpected that the reaction could be made the basis of an efficient method for removing H₂S from gas mixtures. Nitrites and/or nitrous acid, in aqueous solutions, are quite susceptible to decomposition into NO and $NO_2$ ($NO_x$) products which, in and of themselves, can pose an environmental problem if the effluent gas is flared and potentially a greater problem if the effluent gas is to be further processed as, for example, in compression stations or the like. However, as can be seen from the data above, if the pH of the aqueous medium is maintained at above 5.5 and preferably above about 6, minimum amounts of $NO_x$ are produced. Environmentally, the amount of $NO_x$ generally produced is below acceptable limits for a gas stream which is to be flared. In the case of an effluent gas stream which is to be processed as, for example, in a compression station, and if the level of $NO_x$ were too high for the particular processing step, the effluent gas can be further treated by well known methods to remove the $NO_x$ or lower it to within acceptable limits.

The foregoing disclosure and description of the invention is illustrative and explanatory thereof, and various changes in the process may be made within the scope of the appended claims without departing from the spirit of the invention.

What is claimed is:

1. A process for removing hydrogen sulfide from a gas mixture comprising treating said gas mixture with an aqueous medium containing an effective amount of a inorganic water soluble metal nitrite at a pH of about 5.5 or greater.

2. The process of claim 1 wherein said gas mixture contains gaseous hydrocarbons.

3. The process of claim 1 wherein said gas mixture comprises natural gas.

4. The process of claim 1 wherein said water soluble nitrite, calculated as nitrite, is present in said aqueous medium in an amount of from about 0.1 percent by weight up to about saturation.

5. The process of claim 1 wherein said water soluble nitrite is selected from the class consisting of alkali metal an alkaline earth-metal nitrites.

6. The process of claim 5 wherein said water soluble nitrite comprises sodium nitrite.

7. The process of claim 1 wherein said aqueous solution is buffered to provide a pH in the range of from about 6 to about 10.

8. The process of claim 6 wherein a buffering agent selected from the class consisting of borates, phosphates, phthalates, bicarbonates, ammonium chloride, and mixtures thereof is present in said aqueous medium.

9. The process of claim 1 wherein said treating comprises scrubbing said gas mixture by passing said gas mixture upwardly through said aqueous medium.

* * * * *

UNITED STATES PATENT AND TRADEMARK OFFICE
CERTIFICATE OF CORRECTION

PATENT NO. : 4,515,759
DATED : May 7, 1985
INVENTOR(S) : Edward E. Burnes
Kishan Bhatia It is certified that error appears in the above—identified patent and that said Letters Patent is hereby corrected as shown below:

In Column 14, line 3, delete "a" and insert therefor --an--.

In Column 14, line 16, delete "an" and insert therefor --and--.

Signed and Sealed this

Second Day of September 1986

[SEAL]

Attest:

DONALD J. QUIGG

Attesting Officer        Commissioner of Patents and Trademarks

REEXAMINATION CERTIFICATE (756th)
United States Patent [19]
Burnes et al.

[11] B1 4,515,759
[45] Certificate Issued  Sep. 8, 1987

[54] PROCESS OF REMOVING HYDROGEN SULFIDE FROM GAS MIXTURES

[75] Inventors: Edward E. Burnes, Arroyo Grande, Calif.; Kishan Bhatia, Katy, Tex.

[73] Assignee: NL Industries, Inc., New York, N.Y.

Reexamination Request:
No. 90/001,066, Aug. 14, 1986

Reexamination Certificate for:
Patent No.: 4,515,759
Issued: May 7, 1985
Appl. No.: 549,274
Filed: Nov. 3, 1983

Certificate of Correction issued Sep. 2, 1986.

[51] Int. Cl.$^4$ ............................................. B01D 53/34
[52] U.S. Cl. .................................. 423/220; 423/223; 423/232; 423/573 R
[58] Field of Search ............... 423/210, 220, 223, 224, 423/234, 385, 573 G, 573 R; 422/4, 5

[56] References Cited

FOREIGN PATENT DOCUMENTS

87135  5/1896  Fed. Rep. of Germany .
10931  of 1896  United Kingdom .

OTHER PUBLICATIONS

Chemical Engineers' Handbook, 5th ed. Perry et al., eds. McGraw-Hill Book Co. 1973, pp. 18-3, 4.
Analytical Chemistry, 3rd ed. Skoog and West, Holt, Rinehart, and Winston, 1979, pp. 197, 201.
Momentum, Heat, and Mass Transfer, 2nd ed. Bennett & Myers, McGraw-Hill Book Co. 1974, pp. 519-521.
CRC Handbook of Chemistry and Physics, 62nd ed, Weast et al., eds. CRC Press, Inc. 1981, pp. B-90, 105.

*Primary Examiner*—Andrew H. Metz

[57] ABSTRACT

Process for the removal of hydrogen sulfide from gas mixtures, particular gas mixtures containing hydrocarbons, wherein the gas mixture is treated with an aqueous solution of a water soluble nitrite such as sodium nitrite, the pH of the aqueous solution being at least 5.5 or greater.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 3, 5 and 6 are cancelled.

Claims 1, 7 and 8 are determined to be patentable as amended.

Claims 4 and 9, dependent on an amended claim, are determined to be patentable.

1. A process for *selectively* removing hydrogen sulfide from a gas mixture comprising treating [said] *a* gas mixture *comprising natural gas, hydrogen sulfide and carbon dioxide* with an aqueous medium containing [an effective amount of a inorganic water soluble metal] *sodium* nitrite, *said aqueous medium being buffered to* [at] a pH of about 5.5 or greater.

7. The process of claim 1 wherein said aqueous [solution] *medium* is buffered to provide a pH in the range of from about [6] *7* to about 10.

8. The process of claim [6] *1* wherein a buffering agent selected from the class consisting of borates, phosphates, phthalates, bicarbonates, ammonium chloride, and mixtures thereof is present in said aqueous medium.

* * * * *

REEXAMINATION CERTIFICATE (1169th)
United States Patent [19]
Burnes et al.

B2 4,515,759
[45] Certificate Issued  Dec. 12, 1989

[54] PROCESS OF REMOVING HYDROGEN SULFIDE FROM GAS MIXTURES

[75] Inventors: Edward E. Burnes, Arroyo Grande, Calif.; Kishan Bhatia, Katy, Tex.

[73] Assignee: NL Industries, Inc., New York, N.Y.

Reexamination Request:
No. 90/001,598, Sep. 2, 1988

Reexamination Certificate for:
Patent No.: 4,515,759
Issued: May 7, 1985
Appl. No.: 549,274
Filed: Nov. 3, 1983

Reexamination Certificate B1 4,515,759 issued Sep. 8, 1987.
Certificate of Correction issued Sep. 2, 1986.

[51] Int. Cl.$^4$ .............................................. B01D 53/34
[52] U.S. Cl. .................................... 423/220; 423/223; 423/232; 423/576.4
[58] Field of Search ............... 423/210, 220, 223, 224, 423/234, 385, 573 G, 573 R; 422/4, 5

[56] References Cited

U.S. PATENT DOCUMENTS

| | | | |
|---|---|---|---|
| 2,665,190 | 1/1959 | Congdon et al. | 423/241 |
| 3,622,273 | 11/1971 | Roberts et al. | 423/576.6 |
| 4,009,251 | 2/1977 | Meuly | 423/576.6 |

FOREIGN PATENT DOCUMENTS

87135  5/1896  Fed. Rep. of Germany.
10931  of 1896  United Kingdom.

OTHER PUBLICATIONS

Certificate of Correction to U.S. Pat. No. 4,515,759.
Chemical Engineers' Handbook, 5th ed., Perry et al, eds., McGraw-Hill Book Co., 1973, pp. 18-3 to 4.
Analytical Chemistry, 3rd ed., Skoog and West, Holt, Rinehart, and Winston, 1979, pp. 197, 201.
Mellor, A Comprehensive Treatise on Inorganic and Theoretical Chemistry, Longmans, Green and Co., 1947, pp. 455–458.
Hackh's Chemical Dictionary, 4th ed., Grant, ed., McGraw-Hill Book Co., 1969, pp. 291-292.
Bennett & Myers, Momentum, Heat, and Mass Transfer, 2nd ed., McGraw-Hill Book Co., 1974, pp. 519–521.
Rose, Condensed Chemical Dictionary, 7th ed., Reinhold Publishing Corp., 1966, pp. 653–654.
Katz et al., Handbook of Natural Gas Engineering, McGraw-Hill Book Co., 1959, pp. 28–29.
Reservoir Engineering Material, Esso Production Research Co., 1966, p. 6.
Bhatia et al, "One-Step Process Takes H$_2$S from Gas Stream", Oil & Gas Journal, Oct. 20, 1986, pp. 44–46, 49.
Bhatia et al, "Examination of Field Data from a New Gas Sweeting Process", presented to Society of Petroleum Engineers in New Orleans, LA; Oct. 5–8, 1986.
McGraw–Hill Dictionary of Scientific and Technical Terms, 2nd ed., Lapedes, ed., McGraw-Hill Book Co., 1978, p. 797.
Karrer, Lehrbuch der Organischen Chemie, Georg Thieme Verlag, 1948, p. 405 (partial translation).
Funk & Wagnalls New Practical Standard Dictionary, Funk & Wagnalls Co., 1952 edition, p. 662.
Comptes Rendus Hebdomadaires des Seances de l'Academe des Sciences, Gauthier-Villars, 1913, pp. 796–799.
Gollmar, "Removal of Sulfur Compounds from Coal Gas", Chemistry of Coal Utilization, 1945, vol. 2, pp. 947, 983.
Encyclopedia of Chemical Technology, Kirk–Othmer, vol. 22, p. 116, Third Edition, 1983.
Encyclopedia of Chemical Technology, Kirk–Othmer, vol. 19, pp. 376–377, Second Edition, 1969.
Inorganic Chemistry, T. Moeller, Second Edition, (Indian) p. 616, 1959.
Inorganic Chemistry, T. Moeller, p. 616, 1952.
Nouveau Traité de Chimie Mineralé, published under direction of Paul Pascal, 1956, pp. 421–422.
Sodium Nitrite, published by Allied Chemical, Nov. 1981.
Sodium Nitrite, data sheet published by E. I. duPont de Nemours & Co., prior to Sep. 14, 1983.

*Primary Examiner*—Jeffrey Edwin Russel

[57] ABSTRACT

Process for the removal of hydrogen sulfide from gas mixtures, particular gas mixtures containing hydrocarbons, wherein the gas mixture is treated with an aqueous solution of a water soluble nitrite such as sodium nitrite, the pH of the aqueous solution being at least 5.5 or greater.

ND 307

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 3, 5, and 6 are cancelled.

Claims 1, 7, and 8 are determined to be patentable as amended.

Claims 4 and 9, dependent on an amended claim, are determined to be patentable.

1. A process for *selectively* removing hydrogen sulfide from a gas mixture comprising treating [said] *a* gas mixture *comprising natural gas, hydrogen sulfide and carbon dioxide* with an aqueous medium containing [an effective amount of a inorganic water soluble metal] *sodium* nitrite, *said aqueous medium being buffered to* [at] a pH of about 5.5 or greater.

7. The process of claim 1 wherein said aqueous [solution] *medium* is buffered to provide a pH in the range of from about [6] *7* to about 10.

8. The process of claim [6] *1* wherein a buffering agent selected from the class consisting of borates, phosphates, phthalates, bicarbonates, ammonium chloride, and mixtures thereof is present in said aqueous medium.

\* \* \* \* \*